(12) United States Patent
Nagarajan et al.

(10) Patent No.: US 11,998,277 B2
(45) Date of Patent: Jun. 4, 2024

(54) OPHTHALMIC IMAGING DEVICE FOR IMAGING POSTERIOR AND ANTERIOR EYE REGIONS

(71) Applicant: REMIDIO INNOVATIVE SOLUTIONS PVT. LTD., Bengaluru (IN)

(72) Inventors: Shanmuganathan Nagarajan, Valangaiman (IN); Anand Sivaraman, Bangalore (IN)

(73) Assignee: REMIDIO INNOVATIVE SOLUTIONS PVT. LTD., Bengalurn (IN)

( * ) Notice: Subject to any disclaimer, the term of this patent is extended or adjusted under 35 U.S.C. 154(b) by 889 days.

(21) Appl. No.: 16/980,918

(22) PCT Filed: Mar. 18, 2019

(86) PCT No.: PCT/IN2019/050217
§ 371 (c)(1),
(2) Date: Sep. 15, 2020

(87) PCT Pub. No.: WO2019/175903
PCT Pub. Date: Sep. 19, 2019

(65) Prior Publication Data
US 2020/0405147 A1    Dec. 31, 2020

(30) Foreign Application Priority Data
Mar. 16, 2018  (IN) .............................. 201841009807

(51) Int. Cl.
*A61B 3/135*    (2006.01)
*A61B 3/00*    (2006.01)
(Continued)

(52) U.S. Cl.
CPC ............ *A61B 3/135* (2013.01); *A61B 3/0008* (2013.01); *A61B 3/12* (2013.01); *A61B 3/132* (2013.01); *A61B 3/158* (2013.01)

(58) Field of Classification Search
CPC .. A61B 3/102; A61B 3/12; A61B 3/14; A61B 3/0025; A61B 3/103; A61B 3/107;
(Continued)

(56) References Cited

U.S. PATENT DOCUMENTS 4,411,502 A * 10/1983 Lang ...................... A61B 3/135
                                                      351/221
4,702,596 A    10/1987 Nohda
(Continued)

FOREIGN PATENT DOCUMENTS

EP         0777142 A2    6/1997
JP      2003047695 A    2/2003
(Continued)

OTHER PUBLICATIONS

International Search Report for PCT/IN2019/050217 dated Jul. 24, 2019, 2 pages.
(Continued)

*Primary Examiner* — Brandi N Thomas
(74) *Attorney, Agent, or Firm* — Cozen O'Connor

(57) ABSTRACT

An ophthalmic imaging device (300) includes a fundus module (210) and a slit lamp 5 module (220) movably coupled to each other. The fundus module (210) includes an illumination module (230) and an imaging module (240). The illumination module (230) is adapted to yield a first partially blocked beam. The imaging module (240) includes a mirror (324) with a hole and an objective lens (326) to produce a reflected first partially blocked beam and a second partially blocked beam, to form a cornea 10 illuminating doughnut (502) and pupil illuminating doughnut (504), (Continued)

respectively, on an anterior region of the eye and form an image of the posterior\\region of the eye on an image plane (346). The slit lamp module (220) is adapted to view and capture the image of anterior and posterior regions of the eye.

14 Claims, 8 Drawing Sheets

(51) Int. Cl.
    *A61B 3/12*     (2006.01)
    *A61B 3/13*     (2006.01)
    *A61B 3/15*     (2006.01)

(58) Field of Classification Search
CPC ..... A61B 3/1005; A61B 3/135; A61B 3/0008; A61B 3/113; A61B 3/0058; A61B 3/117; A61B 2018/2025; A61B 3/10; A61B 2018/20359; A61B 3/0075; A61B 2018/2035; A61B 2018/2266; A61B 2018/2272; A61B 3/1241; A61B 3/1015; A61B 2017/00973; A61B 3/1233; A61B 3/0033; A61B 3/0091; A61B 3/1208; A61B 3/13; A61B 3/152; A61B 2017/00694; A61B 3/1225; A61B 3/18; A61B 2017/00199; A61B 18/20; A61B 3/0041; A61B 3/0083; A61B 3/1173; A61B 3/132; A61B 3/158; A61B 5/0066; A61B 2017/00123; A61B 2018/00636; A61B 2034/742; A61B 3/022; A61B 3/16; A61B 5/489; A61B 5/4893; A61B 3/024; A61B 3/028; A61B 3/06; A61B 3/1025; A61B 3/15; A61B 3/154; A61B 3/156; A61B 18/203; A61B 2018/00577; A61B 2018/00613; A61B 2018/00642; A61B 2018/00785; A61B 2018/00904; A61B 2018/20351; A61B 2018/20355; A61B 3/032; A61B 3/04; A61B 3/063; A61B 3/125; A61F 9/008; A61F 2009/00863; A61F 9/00821; A61F 2009/00897; A61F 9/00823; A61F 2009/00878; A61F 2009/00846; A61F 2009/00872; A61F 2009/00882; A61F 2009/0087; A61F 9/00802; A61F 9/00825; A61F 2009/0035; A61F 9/00804; A61F 2009/00868; A61F 2009/00876; A61F 2009/00889; A61F 9/009; A61F 2009/00851; A61F 2009/00865; A61F 2009/00895; A61F 9/0026; A61F 9/00838; A61F 9/045; A61F 2/1627; A61F 2/1635; A61F 2/1637; A61F 2/1659; A61F 2009/00848; A61F 2009/00859; A61F 2009/0088; A61F 2009/00887; A61F 9/00; A61F 9/0017; A61F 9/00806; A61F 9/00812; A61F 9/00817; A61F 9/00827; A61F 9/08

See application file for complete search history.

(56) References Cited

U.S. PATENT DOCUMENTS

| | | | | |
|---|---|---|---|---|
| 6,520,640 B1* | 2/2003 | Binnun | ............... | A61B 3/14 351/206 |
| 2009/0244483 A1* | 10/2009 | Yoshino | ............... | A61B 3/14 351/206 |
| 2012/0257166 A1* | 10/2012 | Francis | ............... | A61B 3/1025 351/208 |
| 2014/0146288 A1* | 5/2014 | Anand | ............... | A61B 3/0008 351/207 |
| 2015/0374233 A1 | 12/2015 | Zhang et al. | | |

FOREIGN PATENT DOCUMENTS

| | | |
|---|---|---|
| JP | 2009095518 A | 5/2009 |
| JP | 2009207590 A | 9/2009 |
| JP | 2011120610 A | 6/2011 |
| WO | 2012176026 A1 | 12/2012 |

OTHER PUBLICATIONS

Written Opinion for PCT/IN2019/050217 dated Jul. 24, 2019, 5 pages.

EP Search Report dated Nov. 5, 2021, in EP App No. 19767834, 1 page.

Examination Report dated Sep. 15, 2021 in corresponding Indian Application No. 201841009807, 5 pages.

Notice of Reasons for Refusal dated Dec. 6, 2022, for Japanese Application No. 2020-549627, 4 pages.

Notice of Reasons for Refusal dated Jul. 6, 2023, for Japanese Application No. 2020-549627, 4 pages.

\* cited by examiner

OPHTHALMIC IMAGING DEVICE FOR IMAGING POSTERIOR AND ANTERIOR EYE REGIONS

TECHNICAL FIELD

The subject matter described herein, in general, relates to an ophthalmic imaging device, and in particular to an ophthalmic imaging device for imaging the posterior and anterior regions of the eye.

BACKGROUND

In ophthalmology, the eye is divided into two main segments: the anterior segment and the posterior segment. The anterior segment refers to the front portion of the eye and includes the iris, conjunctiva, and lens. The posterior segment is the portion of the eye behind the lens and includes the retina and various linings and nerves. Generally, an ophthalmic examination uses a slit lamp device to examine the posterior and anterior regions of the eye. The slit lamp allows the use of different illumination levels ranging from a broad pattern to a narrow-slit pattern. The narrow-slit pattern can be used to specifically illuminate and isolate different parts of the eye in different images.

Currently, doctors use additional ocular or aspheric lenses along with the slit lamp to observe a patient's eyes. However, this method results in an extremely small field of view and poor image quality, as the images have corneal and ocular reflection artefacts. Hence, it is also not possible to obtain photo-documentation, i.e., capture and save images, of the examination done for future reference.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Current techniques for examining the eye, generally use a slit lamp device to observe and image the anterior portions of the eye. When the posterior regions of the eye are to be examined, a separate ocular lens is placed close to the patient's eye and in front of the slit lamp device.

Figure 1:
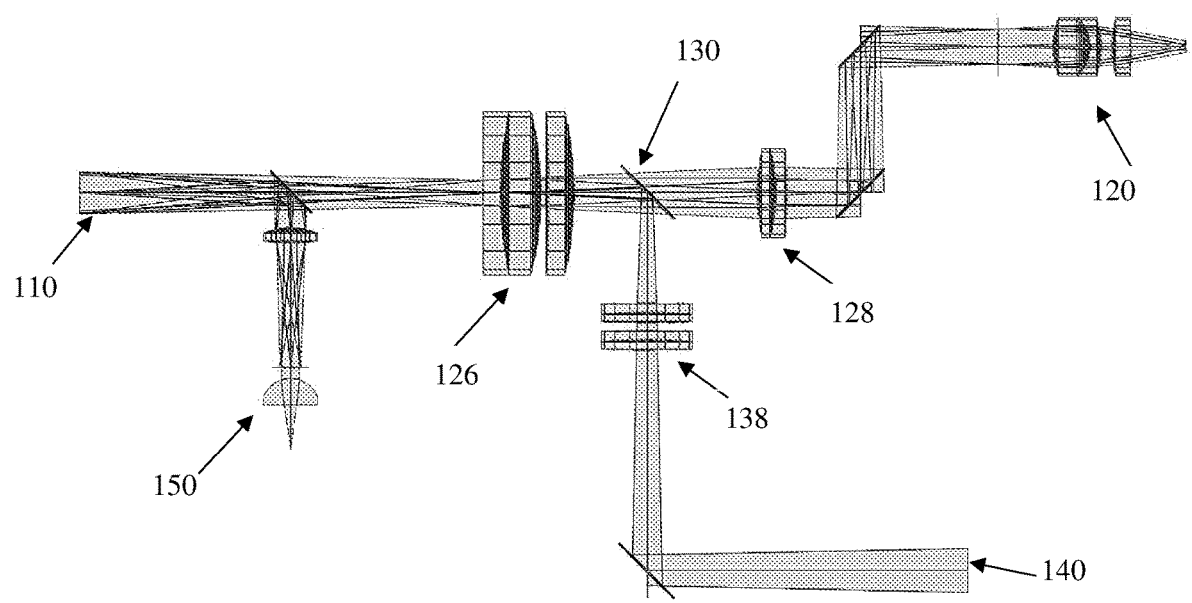
FIG. 1(a) illustrates a conventional slit lamp device used for imaging the anterior regions of the eye.
FIG. 1(b) illustrates a conventional slit lamp device used in conjunction with a separate ocular lens for imaging the posterior regions of the eye.
Figure 1:
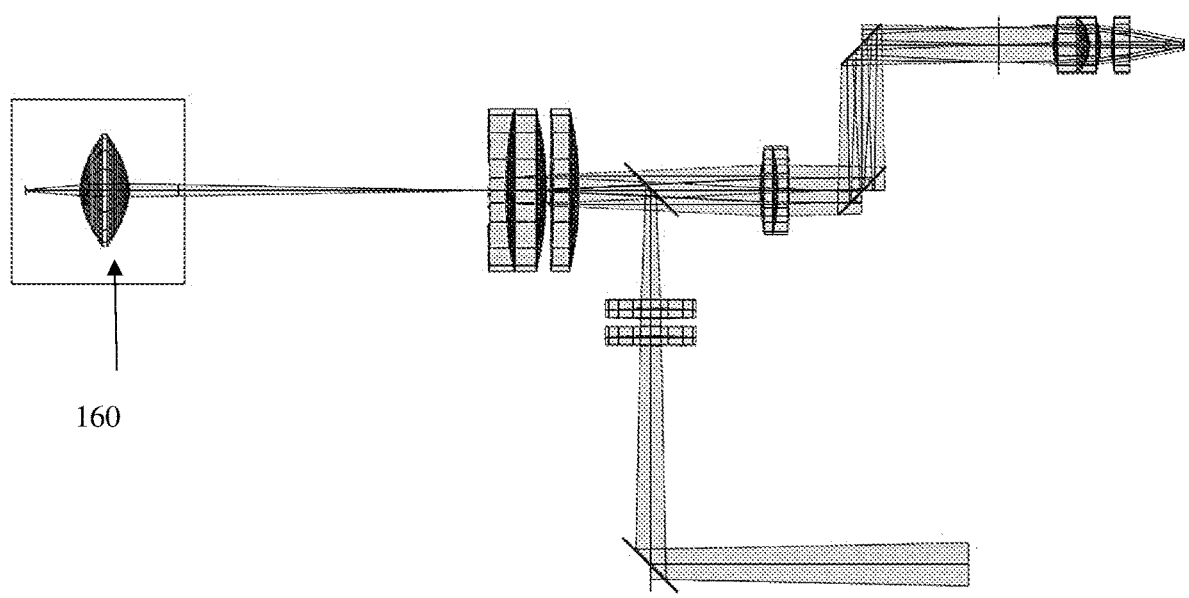

FIG. 1(a) illustrates a conventional slit lamp device used for imaging the anterior regions of the eye. The eye, on a side 110, is illuminated using a light source 150. The image of the anterior regions of the eye are viewed on an opposite side through an eyepiece 120. A beam splitter 130 is placed between a collimating lens 126 and a converging lens 128. The beam splitter 130 allows the reflected beam to be split into two portions. One portion is used for capturing and recording images using a camera 140 via camera lens 138. The second portion is used for viewing the image on the eyepiece 120. FIG. 1(b) illustrates a conventional slit lamp device used in conjunction with a separate ocular lens 160 for imaging the posterior regions of the eye.

However, using the extra lens and the slit lamp device to observe the posterior regions allows only a limited field of view of about 15°. Further, extraneous reflections from the anterior and posterior regions of eye do not allow for increasing the field of view, and images observed hence are fuzzy. The field of view obtained is also limited by the imaging optics of the slit lamp setup used. For example, even if an ocular lens of small focal length is used, the field of view of the posterior regions cannot be increased much because the optics of the slit lamp device cannot be changed. In addition, two separate devices, in the form of a slit lamp device and an extra ocular lens are required for imaging the anterior and the posterior regions, respectively, of the eye.

Furthermore, it is desirable to be able to record images from ophthalmic examination for future reference. However, it is currently not done because of the poor quality of images resulting from corneal and ocular reflection artefacts.

The present subject matter relates to an ophthalmic imaging device that can image both the anterior and posterior sections of the eye, without the use of an external lens or external combination of lenses. The posterior regions of the eye can be viewed in wide field using the device. The device also helps in simultaneously viewing and capturing images of the region (anterior or posterior) being examined using the same eyepiece and camera arrangement for both regions without loss of field of view or clarity and with minimal artefacts.

The following is a detailed description of the present subject matter with reference to the accompanying figures. It should be noted that the description merely illustrates the principles of the present subject matter. It will thus be appreciated that those skilled in the art will be able to devise various arrangements that, although not explicitly described herein, embody the principles of the present subject matter and are included within its scope. Furthermore, all examples recited herein are intended only to aid the reader in understanding the principles of the present subject matter. Moreover, all statements herein reciting principles, aspects and implementations of the present subject matter, as well as specific examples thereof, are intended to encompass equivalents thereof.

Figure 2:
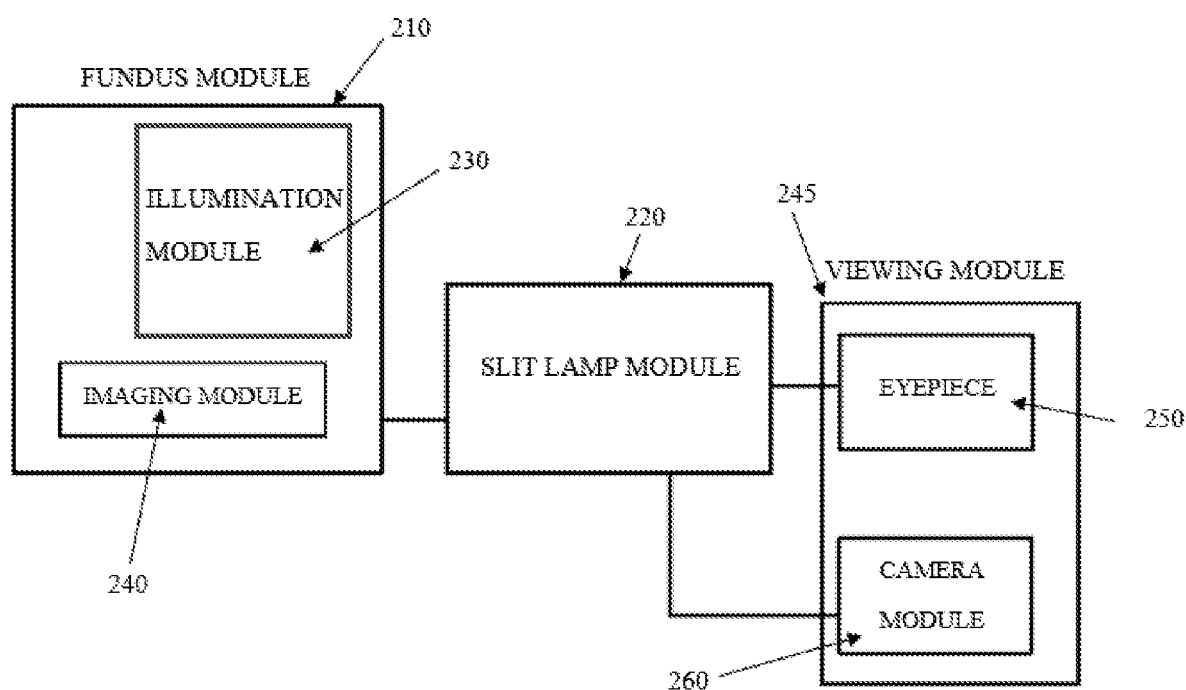
FIG. 2 is a block diagram of an example ophthalmic imaging device, in accordance with an implementation of the present subject matter.

FIG. 2 is a block diagram of the ophthalmic imaging device, in accordance with an implementation of the present subject matter. The ophthalmic imaging device includes a fundus module 210 and a slit lamp module 220 which are movably coupled together. The coupling can be provided using any methods known in the art, such as linear movement hinges, rotating hinges, etc. The fundus module 210 includes an illumination module 230 and an imaging module 240. The imaging module 240 is coupled to the slit lamp module 220 such that the imaging of the posterior and anterior regions of the eye is performed using the single ophthalmic imaging device, which can be observed using a viewing module 245. The viewing module 245 may include an eyepiece 250 and a camera module 260. The images can be viewed via the eyepiece 250 and images can be recorded and captured using the camera module 260 simultaneously, allowing the images seen by the doctor to be stored for future reference.

Figure 3:
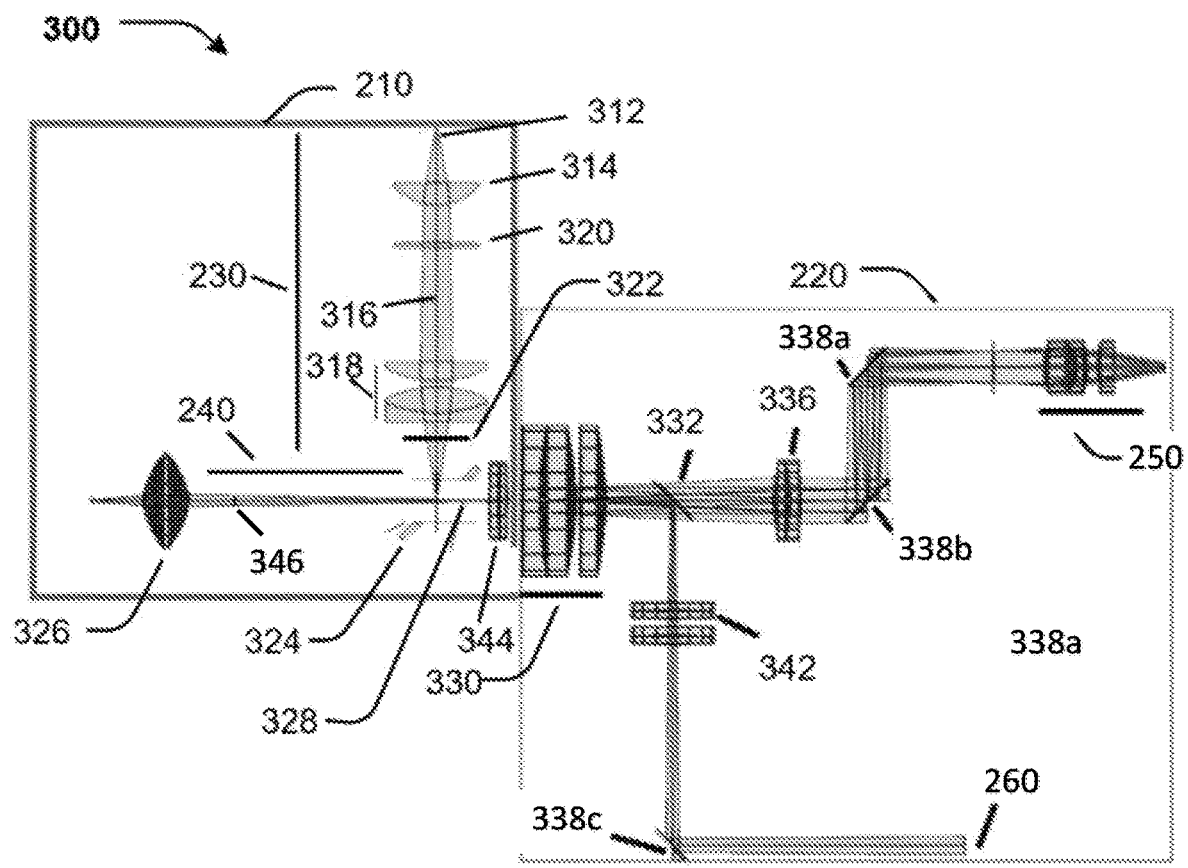
FIG. 3 illustrates an example ophthalmic imaging device, in accordance with an implementation of the present subject matter.

FIG. 3 depicts an example ophthalmic imaging device, in accordance with an implementation of the present subject matter. The ophthalmic imaging device 300 includes a fundus module 210 and a slit lamp module 220. The fundus module 210 and the slit lamp module 220 are movably coupled together. The coupling can be provided using any methods known in the art, such as linear movement hinges, rotating hinges, etc. The fundus module 210 includes an illumination module 230 and an imaging module 240.

The illumination module 230 includes a light source 312. The light source 312 may be one of an LED, a halogen lamp, and a laser light source, or any other light sources known in the art. A condenser lens 314 is placed in front of the light source 312 at a spaced apart distance from the light source 312 and along an illumination axis 316. The condenser lens 314 condenses the light emanating from the light source 312 to provide a condensed beam. The condensed beam is focused using a projection lens system 318 to provide a focused beam along the illumination axis 316. A diffuser 320 may also be placed after the light source. In one example, the diffuser is placed between the condenser lens 314 and the projection lens system 318. The diffuser 320 may include a light absorber. In one example, the light absorber is a black dot placed on the diffuser 320. The light absorber helps in reducing extraneous reflections from the eye when imaging.

The illumination module 230 includes a shield 322 which is placed at a spaced apart distance from the projection lens system 318 along the illumination axis 316. The shield 322 blocks a part of the light emanating from the projection lens system 318 to yield a first partially blocked beam on an imaging axis 328 of the imaging module 240.

The imaging module 240 comprises a mirror 324, diopter correcting lens 344, and at least one objective lens 326 along the imaging axis 328, wherein the imaging axis 328 is perpendicular to the illumination axis 316. In one embodiment of the present subject matter, the mirror 324 has one hole for uniocular or monocular viewing via the viewing module 245. As used herein, the terms uniocular and monocular are used interchangeably. In another embodiment, the mirror 324 has two holes for binocular or stereoscopic viewing via the viewing module 245. As used herein, the terms binocular and stereoscopic are used interchangeably. The mirror 324 is placed at an angle to the illumination axis 316. In an example, the angle can be varied according to the design of the ophthalmic imaging device (300).

The first partially blocked beam from the illumination module 230 is incident on a first side of the mirror 324 to produce, on reflection, a reflected first partially blocked beam and a second partially blocked beam along the imaging axis 328. The reflected first partially blocked beam and second partially blocked beam form a cornea illuminating doughnut and pupil illuminating doughnut, respectively. The cornea illuminating doughnut is formed on the corneal plane, which is on the anterior region of the eye and the pupil illuminating doughnut is formed on the pupil plane, which is also on the anterior region of the eye. The cornea illuminating doughnut is formed because of reflection of the first partially blocked beam from the mirror 324, because of the presence of the shield 322. The pupil illuminating doughnut is formed because of reflection of light from the mirror 324 and the hole of the mirror. Thus, the cornea illuminating doughnut corresponds to an image of the projection lens system 318 and the shield 322. The pupil illuminating doughnut corresponds to an image of the mirror 324 and the hole of the mirror 324. Since the shield 322 and the mirror 324 are at different distances from the light source 312, the images formed by the reflected first partially blocked beam and the second partially blocked beam are formed at two different parallel planes.

In an embodiment, the mirror 324 with a single hole is used in the ophthalmic imaging device 300 to view a monocular image of the posterior region of the eye. If a mirror 324 with two holes is used, then a stereoscopic image of the posterior region of the eye can be observed, as explained below with reference to FIG. 7.

The cornea illuminating doughnut and pupil illuminating doughnut are projected on the eye through an objective lens 326. The cornea illuminating doughnut and pupil illuminating doughnut are formed on two parallel planes, i.e., the corneal plane and the pupil plane, on the eye. The cornea and pupil illuminating doughnuts have an outer region, formed between an outer circle and an inner circle, and an inner region formed within the inner circle. The cornea and pupil illuminating doughnuts are explained below with reference to FIG. 6.

The outer regions of both the cornea and pupil illuminating doughnuts allow the light to be incident on a posterior region of the eye. The posterior region of the eye includes a retina, fovea, choroid etc. Further, once the light falls on the posterior region of the eye, then reflected light from the posterior region of the eye passes through the inner region of the cornea and pupil illuminating doughnuts towards the objective lens 326 and forms an image on an image plane 346. The image formed on the image plane 346 is an image of the posterior region of eye. The distance between the objective lens 326 and the eye being examined can be varied to determine the field of view and the location of the image plane 346 along the illumination axis 316.

The objective lens 326 is placed between the eye and the diopter correcting lens 344. In one example, the objective lens 326 may include a light absorber, which can help reduce extraneous reflections. The light absorber may be in the form of a black dot. The diopter correcting lens 344 allows changing the viewing focus of the image formed on the image plane 346, when viewing using the viewing module 245. The diopter correcting lens 344 is placed at a spaced apart distance from a second side of the mirror 324, opposite the first side of the mirror 324, for adjusting the viewing focus of the posterior image of the eye. The diopter correcting lens 344 is adapted to adjust the viewing focus based on the changing focus of the eye and based on the viewing module 245. For example, when an incident light from the fundus module 210 falls on the posterior region of an eye with myopia or hyperopia, then the image of the posterior region may be formed at different locations such that the location of the image plane 346 on the imaging axis 328 is different compared to the location of the imaging plane 346 for a normal eye. Furthermore, the image in the case of an eye with a disorder may be shifted above or below the imaging axis 328. In this case, the diopter correcting lens 344 adjusts the viewing focus based on the deviation of the image to view the image of posterior region of eye. The adjustment can be done manually or automatically.

In an embodiment, the diopter correcting lens 344 may be a combination of singlet or multi-element lenses which is adapted to provide a magnified field of view of the image of posterior region of eye, to an eyepiece in the slit lamp module 220.

The ophthalmic imaging device 300 further includes the slit lamp module 220. The slit lamp module 220 includes a collimating lens system 330 to allow for viewing and capturing the images of the posterior or anterior regions of the eye. The slit lamp module 220 further includes a beam splitter 332 that splits the light corresponding to the image of a portion (anterior or posterior) of the eye into two split beams. A first split beam of the image of the portion of the eye goes to the eyepiece 250 of the viewing module 245 via one or more converging lenses 336 and a first set of reflecting mirrors 338a and 338b for viewing the images. A second split beam of the image of the portion of the eye goes to the camera module 260 via the camera lens 342 and a second set of reflecting mirrors 338c to capture and record the images. It will be understood that any camera, such as a mobile phone camera, a digital camera, a DSLR, or the like may be used in the camera module. The axis along which the set of collimating lenses 330, beam splitter 332, and converging lenses are place is also referred to as a slit lamp imaging axis. The slit lamp imaging axis is aligned to the imaging axis 328 of the fundus module 210.

Furthermore, the slit lamp module 220 can be moved along the imaging axis 328 towards or away from the eye. The linear movement of the slit lamp module 220 can increase or decrease the field of view of the eye by moving toward or away from the eye, respectively. The linear movement of the slit lamp module can change the viewing focus. The diopter correcting lens 344 can then adjust the viewing focus to compensate for the change in the focus upon the linear movement of the slit lamp module 220.

The fundus module 210 is movably coupled to the slit lamp module 220 wherein the fundus module 210 can be moved away from the slit lamp imaging axis to enable imaging the anterior regions of the eye. In one example, the fundus module 210 is rotated and can be placed above slit lamp module 220. In another example, the fundus module 210 can be rotated and moved away linearly from the slit lamp module 220.

Thus, in operation, for viewing and capturing the image of the posterior region of the eye, the fundus module 210 and the slit lamp module 220 may be aligned serially and used together, while for viewing and capturing the image of the anterior region, the slit lamp module 220 alone may be used. A separate illumination source may be used with the slit lamp module 220 for viewing and capturing the image of the anterior region and in this case, the slit lamp module 220 may work as in conventional devices as discussed earlier with reference to FIG. 1(*a*).

Figure 4A:
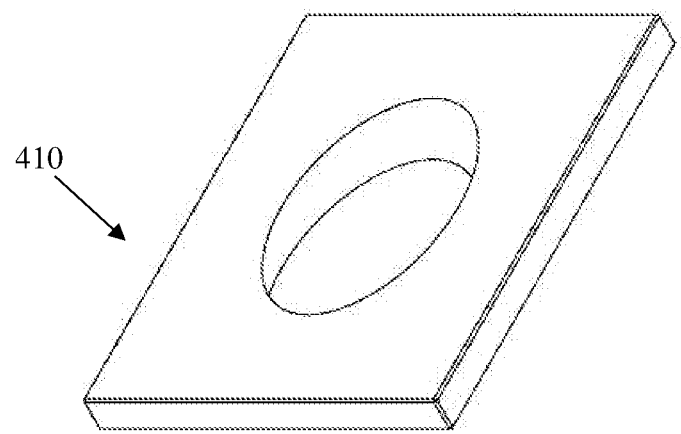
FIG. 4(a) illustrates a mirror for uniocular viewing and FIG. 4(b) illustrates a mirror for binocular viewing, in accordance with an embodiment of the present subject matter.
Figure 4B:
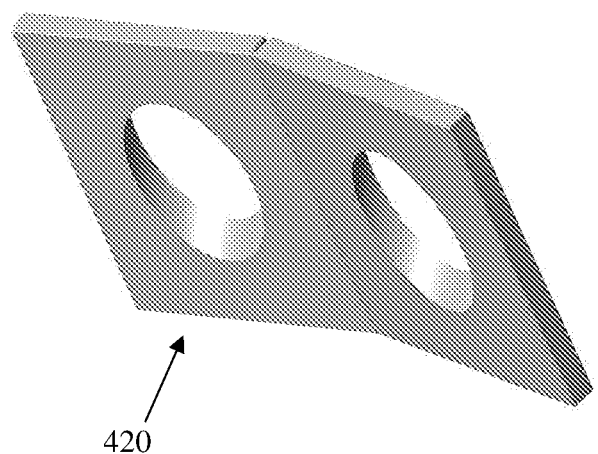

FIG. 4(*a*) illustrates a uniocular mirror and FIG. 4(*b*) illustrates a binocular mirror, in accordance with an embodiment of the present subject matter. The uniocular or monocular mirror 410 is a mirror with a single hole for viewing the image of eye using a uniocular eyepiece. The binocular mirror 420 is a mirror with two holes for viewing the image of the eye using a binocular eyepiece. The uniocular or binocular mirrors are placed along the imaging axis 328 and, at an angle to the illumination module 230 of the fundus module 210. In one example, the mirror 324 may be placed at an angle of 45° to the imaging axis 328. In other examples, the angle may be varied.

Figure 5A:
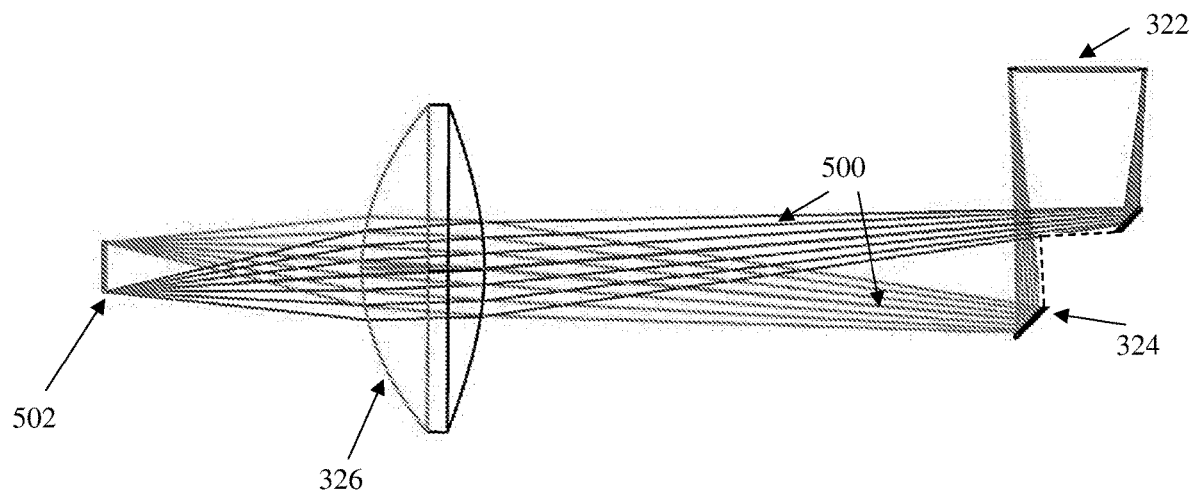
FIG. 5(a) illustrates a cornea illuminating doughnut and FIG. 5(b) illustrates pupil illuminating doughnut on the eye, in accordance with an embodiment of the present subject matter.
Figure 5B:
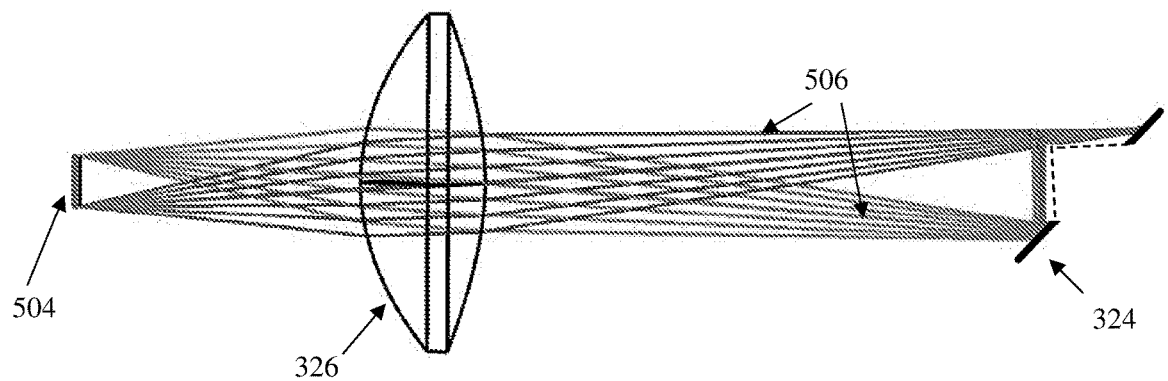

FIG. 5(*a*) illustrates a cornea illuminating doughnut projected on the eye, in accordance with one embodiment of the present subject matter. As shown in FIG. 5(*a*), the shield 322 of the illumination module 230 blocks a part of the light emanating from the projection lens system 318 (not shown in figure) to yield a first partially blocked beam on an illumination axis 316 of the illumination module 230. The first partially blocked beam is incident on a first side of the mirror 324 to produce a reflected first partially blocked beam 500 along the imaging axis 328 to form a cornea illuminating doughnut 502. In one example, the cornea illuminating doughnut 502 is an image formed because of the shield 322. Further, the cornea illuminating doughnut 502 is projected on the eye through an objective lens 326. The cornea illuminating doughnut 502 is formed such that it is focused on the cornea, which is on the anterior region of the eye.

FIG. 5(*b*) illustrates a pupil illuminating doughnut projected on the eye, in accordance with one embodiment of the present subject matter. As shown in FIG. 5(*b*), the first partially blocked beam from the illumination module 230 is incident on a first side of the mirror 324 to produce a second partially blocked beam 506, both along the imaging axis 328. The second partially blocked beam 506 forms a pupil illuminating doughnut 504 on the imaging axis 328. In one example, the pupil illuminating doughnut 504 is an image formed on the pupil because of the mirror 324. The pupil illuminating doughnut 504 is projected on the eye through an objective lens 326. The pupil illuminating doughnut 504 is formed such that it is focused on the pupil, on the anterior region of the eye. The cornea illuminating doughnut 502 as shown in FIG. 5(*a*) and the pupil illuminating doughnut 504 are formed on two parallel planes, i.e., the corneal plane and the pupil plane, on the eye, as explained before.

Figure 6:
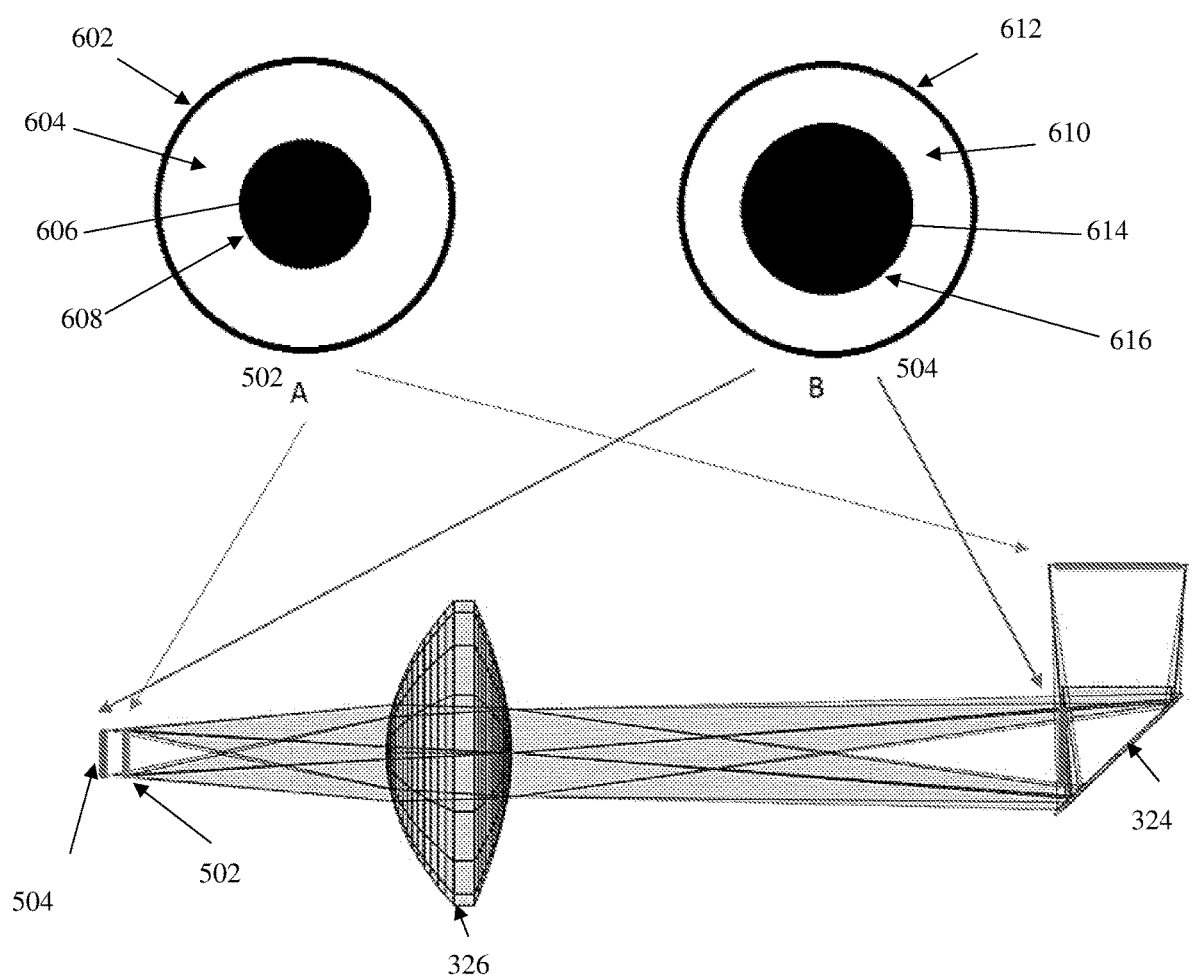
FIG. 6 illustrates a front view of a cornea illuminating doughnut and a pupil illuminating doughnut, in accordance with an embodiment of the present subject matter.

FIG. 6 illustrates a front view of the cornea illuminating doughnut and pupil illuminating doughnut, in accordance with an embodiment of the present subject matter. The front view of the cornea illuminating doughnut 502 comprises an outer region 604 formed between an outer circle 602 having an outer diameter and an inner region 608 formed between an inner circle 606 having an inner diameter. The outer diameter of the projection lens system 318 (not shown in the figure) and the outer dimension of the shield 322 of illumination module 230 forms the outer region 604 and the inner region 608 of the cornea illuminating doughnut, respectively.

Similarly, the front view of the pupil illuminating doughnut 504 comprises an outer region 610 formed between an outer circle 612 having an outer diameter and an inner region 614 formed between an inner circle 616 having an inner diameter. The outer dimension of the mirror 324 and the outer diameter of the hole of the mirror 324 forms the outer region 610 and the inner region 614 of the pupil illuminating doughnut 504, respectively. The sizes of the cornea illuminating doughnut 502 and pupil illuminating doughnut 504 can be varied by changing the dimensions of the respective projection lens system 318, shield 322, mirror 324 and the size of the hole.

Figure 7:
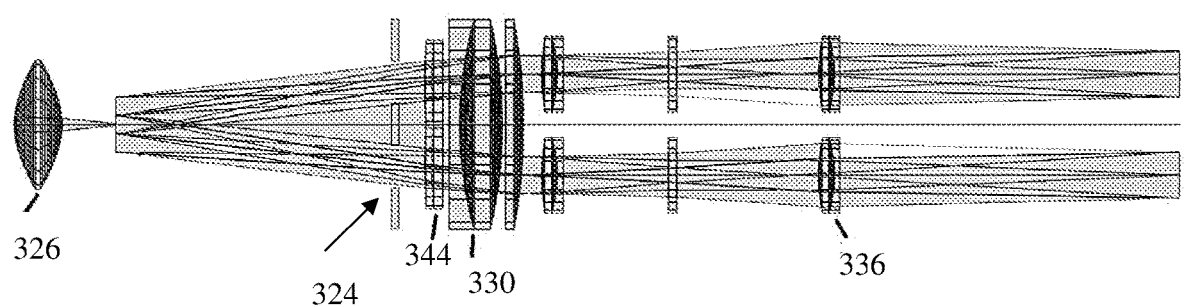
FIG. 7 illustrates a top view of an imaging axis with the binocular mirror for producing a stereoscopic image of the eye, in accordance with an embodiment of the present subject matter.

FIG. 7 illustrates a top view of an imaging axis comprising a binocular mirror 420 for producing a stereoscopic image of the eye, in accordance with an embodiment of the present subject matter. In an example, the binocular mirror 420 is used in the ophthalmic imaging device 300 to view stereoscopic images of posterior region of the eyes. The stereoscopic images can be viewed via collimating lens 330 and converging lens 336 by the eyepiece 250 of the viewing module 245.

The ophthalmic device 300 of the present subject matter can be used to capture images with a wide field of view, such as, 50°, and can obtain still and video images in the mydriatic and non-mydriatic conditions. Imaging can be conveniently switched to the anterior or posterior regions of the eye, as and when needed. In one embodiment, the anterior region of the eye can be imaged via the slit lamp module 220 by moving the fundus module 210 out of the imaging axis 328.

Thus, the ophthalmic imaging device 300 of the present subject matter has a modular design enabling both anterior and posterior imaging of the eye. Moreover, the device allows to capture and storage the images using a camera for documentation and future reference.

Although embodiments for an ophthalmic imaging device are described in language specific to structural features, it is to be understood that the present subject matter is not necessarily limited to the specific features described. Rather, the specific features are disclosed as example embodiments for implementing the present subject matter.

We claim:

1. An ophthalmic imaging device for imaging a posterior and an anterior region of an eye, the device comprising:
   a fundus module comprising:
      an illumination module adapted to yield a first partially blocked beam along an illumination axis; and
      an imaging module aligned along an imaging axis, wherein the imaging axis is perpendicular to the illumination axis, the imaging module comprising:
      a mirror with a hole, the mirror being placed at an angle to the illumination axis, wherein the first partially blocked beam is incident on a first side of the mirror to produce a reflected first partially blocked beam and a second partially blocked beam along the imaging axis;
      at least one objective lens adapted to focus the reflected first partially blocked beam and the second partially blocked beam received from the first side of the mirror, to produce a cornea illuminating doughnut and a pupil illuminating doughnut, respectively, on the cornea and pupil of the eye, and form an image of the posterior region of the eye on an image plane; and
      a diopter correcting lens placed at a distance from a second side of the mirror along the imaging axis for adjusting a viewing focus of the image of the posterior region of the eye; and
   a slit lamp module adapted to view and capture the image of the posterior region of the eye through the diopter correcting lens, wherein the slit lamp module and the fundus module are movably coupled to each other, and wherein the diopter correcting lens is adapted to adjust the viewing focus to compensate for one or more of a shift in the image plane, change in the focus upon a linear movement of the slit lamp module, and a viewing module.

2. The ophthalmic imaging device as claimed in claim 1, wherein the illumination module comprises:
   a light source to provide an incident beam along the illumination axis;
   a condenser lens placed at a spaced apart distance from the light source for condensing incident beam and emanating a condensed incident beam;
   a diffuser placed at a spaced apart distance from the condenser lens, wherein the diffuser includes a light absorber for reducing extraneous reflections during imaging;
   at least one projection lens system to focus the condensed incident beam along the illumination axis; and
   a shield placed at a spaced apart distance from the projection lens system to yield the first partially blocked beam along the illumination axis.

3. The ophthalmic imaging device as claimed in claim 1, wherein the each of the cornea illuminating doughnut and pupil illuminating doughnut has an outer region formed between an outer circle having an outer diameter and an inner circle having an inner diameter, and an inner region formed within the inner circle.

4. The ophthalmic imaging device as claimed in claim 3, wherein the cornea illuminating doughnut corresponds to an image of the projection lens system and the shield.

5. The ophthalmic imaging device as claimed in claim 3, wherein the pupil illuminating doughnut corresponds to an image of the mirror and the hole of the mirror.

6. The ophthalmic imaging device as claimed in claim 3, wherein the cornea illuminating doughnut and pupil illuminating doughnut are formed on a corneal plane and pupil plane, respectively, wherein the corneal plane and pupil plane are parallel to each other.

7. The ophthalmic imaging device as claimed in claim 3, wherein the outer regions of the cornea and pupil illuminating doughnuts allow a light to be incident on the posterior region of the eye.

8. The ophthalmic imaging device as claimed in claim 7, wherein a reflected light from the posterior region of the eye passes through the inner regions of the cornea and pupil illuminating doughnuts and through the objective lens to form the image of the posterior region of the eye on the image plane on the imaging axis.

9. The ophthalmic imaging device as claimed in claim 1, wherein the mirror has a single hole for uniocular viewing or two holes for binocular viewing of the image.

10. The ophthalmic imaging device as claimed in claim 1, wherein the diopter correcting lens is a singlet, multi-element lenses or a combination thereof.

11. The ophthalmic imaging device as claimed in claim 2, wherein the light source is one of a LED, a halogen lamp, and a laser light source.

12. The ophthalmic imaging device as claimed in claim 1, wherein the slit lamp module and fundus module are movably coupled to allow the fundus module to be moved away from a slit lamp imaging axis for imaging the anterior region of the eye, wherein the slit lamp imaging axis is aligned to the imaging axis of the fundus module.

13. The ophthalmic imaging device as claimed in claim 12, wherein the slit lamp module is adapted to move linearly along the slit lamp imaging axis to change a field of view of the eye.

14. The ophthalmic imaging device as claimed in claim 1, wherein the slit lamp module comprises:
   a collimating lens system to allow a beam corresponding to an image of a portion of the eye into the slit lamp module;
   a beam splitter for splitting the beam into two split beams, wherein a first split beam is passed to an eyepiece via one or more converging lenses and a first set of reflecting mirrors and a second split beam is passed to a camera module via a camera lens and a second set of reflecting mirrors;
   the eyepiece for viewing the image of the portion of the eye; and
   the camera module for capturing and recording the image of the portion of the eye.

* * * * *